United States Patent [19]

Woodruff

[11] Patent Number: 5,369,120

[45] Date of Patent: * Nov. 29, 1994

[54] PHARMACEUTICAL COMPOSITION OF 7-((SUBSTITUTED)AMINO-8-((SUBSTITUTED)CARBONYL)-(METHYLAMINO)-1-OXASP IRO(4,5)DECANES AND L-DOPA

[75] Inventor: Geoffrey N. Woodruff, Dassels Braughing, Nr. Ware, United Kingdom

[73] Assignee: Warner-Lambert Company, Morris Plains, N.J.

[*] Notice: The portion of the term of this patent subsequent to May 31, 2011 has been disclaimed.

[21] Appl. No.: 98,979

[22] Filed: Jul. 28, 1993

[51] Int. Cl.5 .................. A61K 31/40; A61K 31/195
[52] U.S. Cl. ..................................... 514/409; 514/567
[58] Field of Search .............. 514/212, 278, 409, 462, 514/567, 414

[56] References Cited

U.S. PATENT DOCUMENTS

| | | | |
|---|---|---|---|
| 3,405,159 | 10/1968 | Krieger et al. | 562/446 |
| 4,737,493 | 4/1988 | Horwell | 514/212 |
| 4,965,278 | 10/1990 | Horwell et al. | 514/414 |
| 4,970,200 | 11/1990 | Birkmayer et al. | 514/52 |
| 5,063,242 | 11/1991 | Horwell et al. | 514/414 |
| 5,190,763 | 3/1993 | Edgren et al. | 424/473 |
| 5,192,550 | 3/1993 | Edgren et al. | 424/473 |
| 5,317,028 | 5/1994 | McKnight et al. | 514/409 |

OTHER PUBLICATIONS

*The Merck Index*, 10th Edition, (1983) pp. 784 and 785; Abstract No. 5298.

Primary Examiner—Marianne M. Cintins
Assistant Examiner—K. Weddington
Attorney, Agent, or Firm—Elizabeth M. Anderson

[57] ABSTRACT

A synergistic pharmaceutical composition of substituted phenoxy-, 1-, and 2-naphthalenyloxy-, indenyl-, indolyl-, benzo[b]furanyl-, and benzo[b]thienylcarboxamides of 7,8-(substituted-diamino)-1-oxaspiro[4.5]decanes and L-DOPA as a composition alleviating the symptoms of Parkinson's disease and/or dystonia. A method of using the pharmaceutical composition is also disclosed.

4 Claims, 1 Drawing Sheet

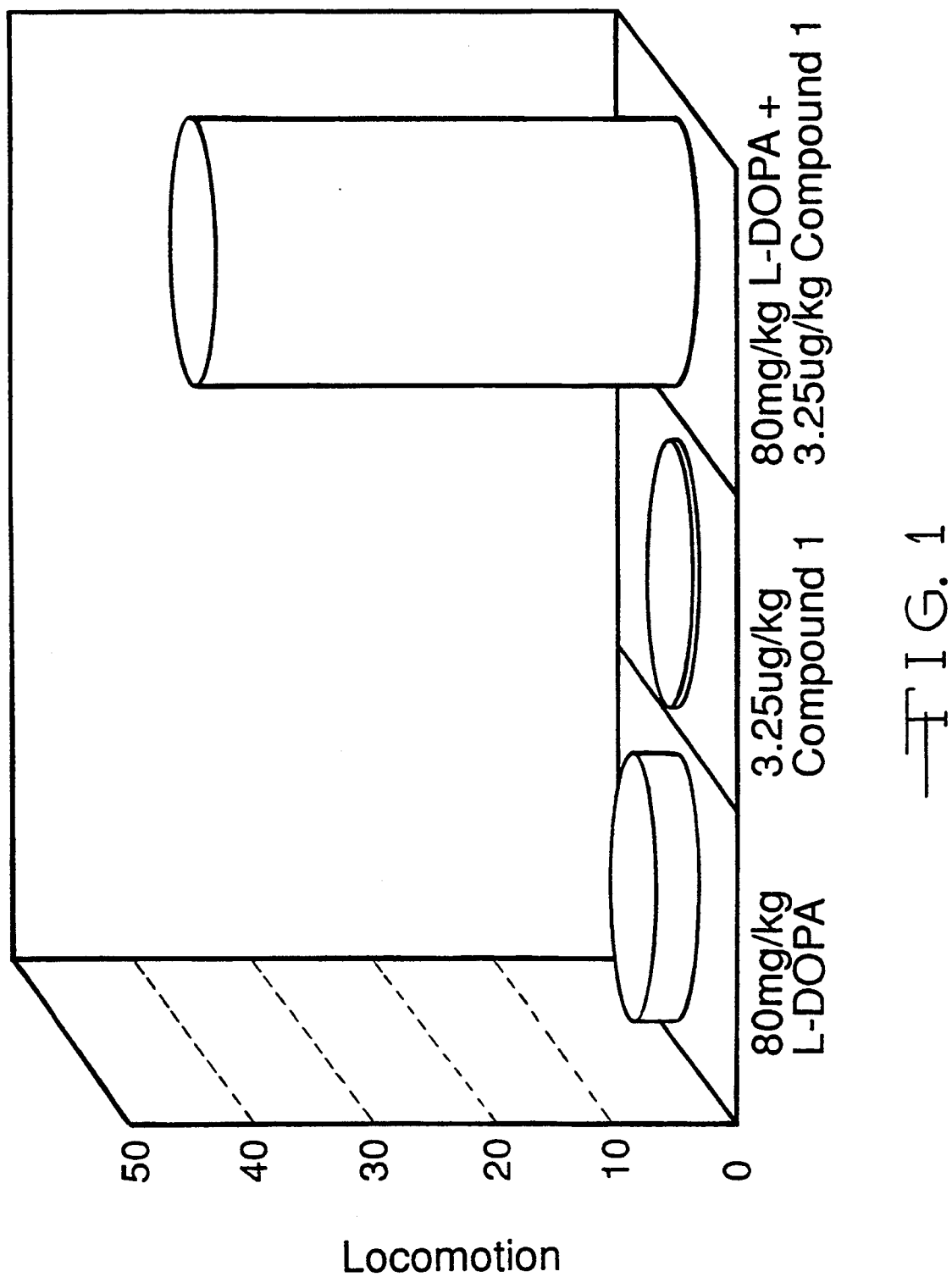

PHARMACEUTICAL COMPOSITION OF 7-((SUBSTITUTED)AMINO-8-((SUBSTITUTED)-CARBONYL)-(METHYLAMINO)-1-OXASPIRO(4,5)DECANES AND L-DOPA

BACKGROUND OF THE INVENTION

The present invention is related to a new pharmaceutical composition having synergistic effects and a method of using 7-((substituted)amino-8-((substituted)carbonyl)(methylamino)-1-oxaspiro(4,5)decanes and the pharmaceutically acceptable salts thereof and L-DOPA as agents useful in treating Parkinson's disease and/or dystonia. The compounds, processes for preparing them, and pharmaceutical compositions containing them are found in U.S. Pat. No. 4,737,493, which is herein incorporated by reference. The disclosed utility in the patent is analgesia. These compounds are also disclosed as having sedative, diuretic, and corticosteroid elevating effects and therefore as being useful diuretic and psychotherapeutic agents.

U.S. Pat. No. 4,965,278 and its divisional 5,063,242 cover use of the above compounds for inflammation, stroke, and cerebrovascular disorders such as cerebral ischemia and infarction. These two patents are hereby incorporated by reference.

Copending application 07/941,576 filed Sep. 8, 1992, covers the use of the compounds in treating Parkinsonism, dystonia, and other movement disorders.

L-DOPA, also known as levodopa, of chemical formula

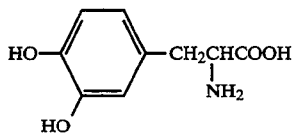

with the chemical name 3-(3,4-dihydroxyphenyl)L-alanine is described in U.S. Pat. No. 3,253,023. This patent teaches a method for recovering the compound from comminuted velvet beans and is hereby incorporated by reference.

U.S. Pat. No. 3,405,159 covers the separation of the compound from the racemate.

U.S. Pat. Nos. 5,192,550 and 5,190,76.3 cover a dosage form for delivering a drug for treating Parkinson's disease. The drugs disclosed are at least one member selected from the group consisting of bromocriptine; bromocriptine and its therapeutically acceptable salts; bromocriptine mesylate; ergot derivatives including lisuride, pergolide, and mesulergine; levodopa; carbidopa; levodopa/carbidopa; amantadine; eldepryl (also known as selegiline); trihexyphenidyl; benztropine; biperiden; ethopropazine; procyclidine; dopamine agonist, monamine, oxidase inhibitors, anticholinergic including benztropine mesylate, trihexyphenidyl hydrochloride, procyclidine hydrochloride, biperiden hydrochloride, and ethopropazine hydrochloride.

Other drugs known in the therapy of the epilepsies, are selected from the group consisting of phenytoin, phenobarbital, diphenylhydantoin sodium, mephenytoin, ethotoin, mephobarbital, primidone, carbamazepine, ethosuximide, methsuximide, phensuximide, valproic acid, trimethadione, paramethadione, benzodiazepine, clonazepam, phenacemide, acetazolamide, and progabide.

U.S. Pat. No. 4,970,200 covers a pharmaceutical composition of the enzyme cofactor nicotinamide adenine dinucleotide in simultaneous administration with L-DOPA.

BRIEF DESCRIPTION OF THE DRAWING

FIG. 1 shows the effect of administration of L-DOPA in the amount of 80 mg/kg, Compound I in the amount of 3.25 μg/kg, and the effect of a combination of the two drugs on the locomotion.

Compound I is (-)-5α-7α-8β-N-methyl-N-[7-(1-pyrrolidinyl)-1-oxaspiro [4.5]dec-8-yl]-4-benzofuranacetamide.

SUMMARY OF THE INVENTION

The present invention relates to a novel pharmaceutical composition which is a synergistic combination of a compound of Formula I and L-DOPA useful in the treatment of Parkinson's disease and/or dystonia.

The invention further relates to a method of treatment comprising administering to a patient in need of such treatment a therapeutically effective amount of a compound of Formula I and of L-DOPA.

A combination of L-DOPA and carbidopa or benzserazide is also expected to be effective in the instant synergistic combination.

DETAILED DESCRIPTION

The present invention provides certain kappa agonists which are in synergistic combination with L-DOPA to provide agents for alleviating Parkinsonian symptoms and/or dystonia. The compounds combined with L-DOPA are

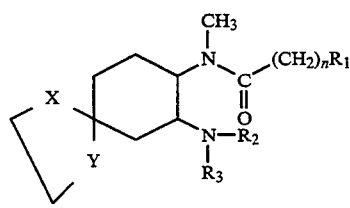

wherein n is an integer of from 1 to 6; either of X or Y is oxygen and the other is —CH$_2$—; R$_1$ is selected from

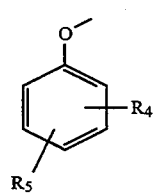

a)

where R$_4$ and R$_5$ are independently hydrogen, fluorine, chlorine, bromine, nitro, trifluoromethyl, alkyl of from 1 to 6 carbon atoms, alkoxy of from 1 to 6 carbon atoms, or aryl;

b) 3,4,5-trimethylphenoxy;

c)

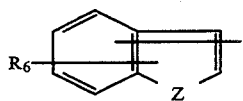

where $R_6$ is hydrogen, fluorine, chlorine, alkyl of from 1 to 6 carbon atoms, or aryl; Z is —CH$_2$—, —O—, —S—, or —NR$_7$— where $R_7$ is hydrogen, alkanoyl of from 1 to 6 carbon atoms, or alkyl of from 1 to 6 carbon atom;

d)

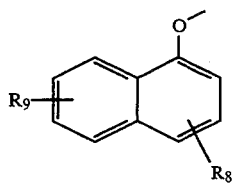

where $R_8$ and $R_9$ are independently hydrogen, fluorine, bromine, alkyl of from 1 to 6 carbon atoms, or alkoxy of from 1 to 4 carbon atoms; or e)

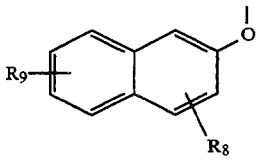

where $R_8$ and $R_9$ are as defined above; $R_2$ is methyl and $R_3$ is hydrogen, alkyl of from 1 to 6 carbon atoms,

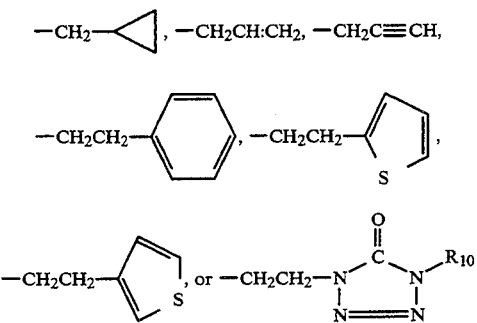

where $R_{10}$ is alkyl of from 1 to 4 carbon atoms; or where $R_2$ and $R_3$ when taken together with the nitrogen atom to which they are attached, form a pyrrolidinyl, piperidinyl, or hexahydro-1H-azepinyl ring; and the pharmaceutically acceptable acid addition salts thereof.

The compounds of the present invention constitute a class of derivatives of certain substituted oxaspiro-diaminocyclohexane compounds of Formula I above in which one nitrogen atom is an amine nitrogen substituted with methyl and a second substituent selected from the group $R_3$ as defined above, or when taken together with the nitrogen atom to which they are attached, $R_2$ and $R_3$ form a pyrrolidinyl, piperidinyl, or hexahydro-1H-azepinyl ring, and the other nitrogen atom is a N-methyl amide nitrogen further substituted with the group $R_1$ as defined above.

Compounds of the present invention contain one or more asymmetric carbon atoms and therefore exist in various stereoisomeric forms. Additionally, the compounds of this invention are capable of existing in different geometric isomeric forms. For example, the oxygen atom of the 5-membered spiro-ring may be positioned on the same side of the average plane of the cyclohexane ring as the amide nitrogen, or on the side opposite. The present invention contemplates all geometric and stereoisomeric forms of the compounds of Formula I above.

The individual stereoisomers are obtained, if desired, from mixture of the different forms by known methods of resolution such as the formation of diastereomers, followed by recrystallization.

Compounds of the instant invention include solyates, hydrates, and salts of Formula I above.

Preferred compounds of the present invention are those of Formula I above wherein $R_1$ is

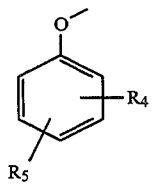

where $R_4$ and $R_5$ are independently hydrogen, fluorine, chlorine, bromine, nitro, trifluoromethyl, alkyl of from 1 to 6 carbon atoms, alkoxy of from 1 to 6 carbon atoms, or aryl.

By the term "aryl" is meant phenyl; phenyl substituted with fluorine, chlorine, alkoxy of from 1 to 4 carbon atoms, nitro, or trifluoromethyl; 2- or 3-thienyl; and 2- or 3-thienyl substituted with alkyl of from 1 to 4 carbon atoms or alkoxy of from 1 to 4 carbon atoms.

Preferred compounds of the present invention are those of Formula I above where R1 is

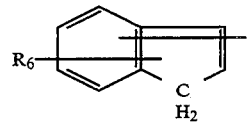

wherein $R_6$ is as defined above. The most preferred compounds are substituted inden-1-yl compounds of Formula I above.

Other preferred compounds of the present invention are those of Formula I wherein $R_1$ is

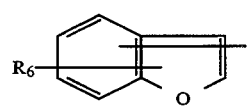

wherein $R_6$ is as defined above. The most preferred compounds are substituted benzofuran-4-yl compounds of Formula I.

Yet other preferred compounds of the present invention are those of Formula I wherein $R_1$ is

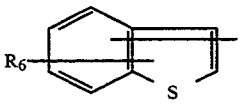

wherein $R_6$ is as defined above. The most preferred compounds are substituted benzo[b]thiophen-4-yl compounds of Formula I.

Yet other preferred compounds of the present invention are those of Formula I wherein $R_1$ is

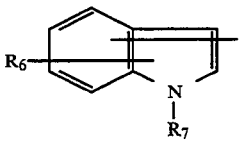

wherein $R_6$ and $R_7$ are as defined above. The most preferred compounds are indol-4-yl compounds of Formula I.

Yet other preferred compounds of the present invention are those of Formula I wherein $R_1$ is

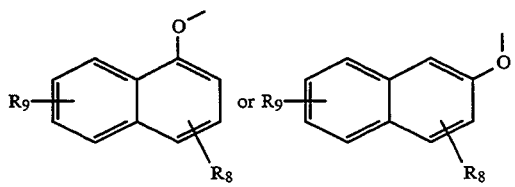

wherein $R_8$ and $R_9$ are independently hydrogen, fluorine, chlorine, bromine, alkyl of from 1 to 4 carbon atoms or alkoxy of from 1 to 4 carbon atoms.

Preferred substituents for $R_2$ and $R_3$ are those where $R_2$ is methyl and $R_3$ is lower alkyl, most preferably methyl, or where $R_2$ and $R_3$ taken together with the nitrogen atom to which they are attached form a pyrrolidinyl ring.

Preferred compounds of the present invention include but are not limited to:

[5R-(5α, 7α, 8β)]-N-Methyl-N-[7-(methyl-2-propynylamino)-1-oxaspiro [4.5]dec-8-yl]-2-phenoxyacetamide,

[5S-(5α, 7α, 8β)]-N-Methyl-N-[7- (methyl-2-propynylamino)-1oxaspiro [4.5]dec-8-yl]-2-phenoxyacetamide,

[5R-(5α,7β,8α)]-N-Methyl-N-[7- (methyl-2-propynylamino)-1-oxaspiro [4.5]dec-8-yl]-2-phenoxyacetamide,

[5S-(5α,7β,8α)]-N-Methyl-N-[7- (methyl-2-propynylamino)-1-oxaspiro [4.5]dec-8-yl ]-2-phenoxyacetamide,

[5R-(5α, 7α, 8β)]-2-(4-Fluorophenoxy)-N-methyl-N-[7-(1-pyrrolidinyl) ]-1-oxaspiro [4.5]dec-8-yl]acetamide,

[5S-(5α, 7α, 8β)]-2-(4-Fluorophenoxy)-N-methyl-N-[7-(1-pyrrolidinyl) ]-1-oxaspiro [4.5]dec-8-yl]acetamide,

[5R-(5α, 7β, 8α)]-2-(4-Fluorophenoxy) -N-methyl-N-[7-(1-pyrrolidinyl) ]-1-oxaspiro [4.5]dec-8-yl]-acetamide,

[5S-(5α, 7β, 8α)]-2-(4-Fluorophenoxy)-N-methyl-N-[7-(1-pyrrolidinyl) ]-1-oxaspiro [4.5]dec-8-yl]acetamide,

[5R-(5α, 7α, 8β)]-2-(4-Fluorophenoxy)-N-methyl-N-[7-[methyl- (2-phenylethyl) amino]-1-oxaspiro[4.5]dec-

[5R-(5α, 7α,8β)]-2-(4-Fluorophenoxy)-N-methyl-N-8-yl]-acetamide,

[5S-(5α, 7α, 8β)]-2-(4-Fluorophenoxy)-N-methyl-N-[7-[methyl- (2 -phenylethyl) amino]-1- oxaspiro [4.5]dec-8-yl ]acetamide,

[5R-(5α, 7β, 8α)]-2-(4-Fluorophenoxy)-N-methyl-N7-[methyl -(2-phenylethyl) amino]-1-oxaspiro[4.5]dec-8-yl ]acetamide,

[5S-(5α, 7β, 8α)]-2-(4-Fluorophenoxy) -N-methyl-N-[7-[methyl-(2-phenylethyl) amino]-1-oxaspiro[4.5]dec-8-yl ]acetamide,

[5R-(5α, 7α, 8β)]-N-Methyl-2-(3-nitrophenoxy)-N-7-(1-pyrrolidinyl)-1-oxaspiro [4.5]dec-8-yl]acetamide,

[5S-(5α, 7α, 8β)]-N-Methyl-2-(3-nitrophenoxy)-N-7-(1-pyrrolidinyl)-1-oxaspiro [4.5]dec-8-yl]acetamide,

[5R-(5α, 7β, 8α)]-N-Methyl-2-(3-nitrophenoxy)-N-7-(1-pyrrolidinyl)-1-oxaspiro [4.5]dec-8-yl]acetamide,

[5S-(5α, 7β, 8α)]-N-Methyl-2-(3-nitrophenoxy)-N-∂8-(1-pyrrolidinyl)-1-oxaspiro [4.5]dec-8-yl]acetamide,

[5R-(5α, 7α, 8β)]-N-Methyl-N-[7-(1-pyrrolidinyl)-1-oxaspiro [4.5]dec-8-yl]-2- [3-(trifluoromethyl)phenoxy]acetamide,

[5S-(5α, 7α, 8β)]-N-Methyl-N-[7-(1-pyrrolidinyl)-1-oxaspiro [4.5]dec-8-yl]-2-[3-(trifluoromethyl) phenoxy]acetamide,

[5R-(5α, 7β, 8α)]-N-Methyl-N-[7-(1-pyrrolidinyl)-1-oxaspiro [4.5]dec-8-yl]-2-[3-(trifluoromethyl)phenoxy]acetamide,

[5S-(5α, 7β, 8α)]-N-Methyl-N-[7-(1-pyrrolidinyl)-1-oxaspiro [4.5]dec-8-yl]-2-[3-(trifluoromethyl)phenoxy]acetamide,

[5R-(5α, 7α, 8β)]-2-(3,4 -Dichlorophenoxy)-N-methyl-N-[7-(1-pyrrolidinyl)-1-oxaspiro [4.5]dec-8-yl]acetamide,

[5S-(5α, 7α, 8β)]-2-(3,4-Dichlorophenoxy)-N-methyl-N-[7-(1-pyrrolidinyl)-1-oxaspiro [4.5]dec -8-yl]-acetamide,

[5R-(5α, 7β, 8α)]-2-(3,4-Dichlorophenoxy)-N-methyl-N-[7-(1-pyrrolidinyl) -1-oxaspiro [4.5]dec-8-yl]-acetamide,

[5S-(5α, 7β, 8α)]-2-(3,4-Dichlorophenoxy)-N-methyl-N-[7- (1-pyrrolidinyl)-1-oxaspiro[4.5]dec-1]-acetamide,

[5R-(5α, 7α, 8β)]-2-(2,6-Dichlorophenoxy)-N-methyl-N-[7-(1-pyrrolidinyl)-1-oxaspiro[4.5]dec-8-yl]-acetamide,

[5S-(5α, 7α, 8β)]-2-(2,6-Dichlorophenoxy)-N-methyl-N-[7-(1-pyrrolidinyl)-1-oxaspiro[4.5]dec-8yl]-acetamide,

[5R-(5α, 7β, 8α)]-2-(2,6-Dichlorophenoxy)-N-methyl-N-[7-(1-pyrrolidinyl)-1-oxaspiro[4.5]dec-8-yl]- acetamide,

[5S-(5α, 7β, 8α)]-2-(2,6-Dichlorophenoxy)-N-methyl-N-[7-(1-pyrrolidinyl)-1-oxaspiro[4.5]dec-8-yl]-acetamide,

[5R-(5α, 7α, 8β)]-2-(3,5-Dichlorophenoxy)-N-methyl-N-[7-(1-pyrrolidinyl)-1-oxaspiro[4.5]dec-8-yl]-acetamide,

[5S-(5α,7α, 8β)]-2-(3,5-Dichlorophenoxy)-N-methyl-N-[7-(1-pyrrolidinyl)-1-oxaspiro[4.5]dec-8-yl]-acetamide,

[5R-(5α, 7β, 8α)]-2-(3,5-Dichlorophenoxy)-N-methyl-N-[7-(1-pyrrolidinyl)-1-oxaspiro[4.5]dec-8-yl]-acetamide,

[5S-(5α, 7β, 8α)]-2-(3,5-Dichlorophenoxy)-N-methyl-N-[7-(1-pyrrolidinyl)-1-oxaspiro[4.5]dec-8-yl]-acetamide,

[5R-(5α, 7α, 8β)]-N-Methyl-2-(1-naphthalenyloxy)-N-[7-(1-pyrrolidinyl)-1-oxaspiro[4.5]dec-8-yl]acetamide,

[5S-(5α, 7α, 8β)]-N-Methyl-2-(1-naphthalenyloxy)-N-[7-(1-pyrrolidinyl)-1-oxaspiro[4.5]dec-8-yl]acetamide

[5R-(5α, 7β, 8α)]-N-Methyl-2-(1-naphthalenyloxy)-N-[7-(1-pyrrolidinyl)-1-oxaspiro[4.5]dec-8-yl]acetamide,

[5S-(5α, 7β, 8α)]-N-Methyl-2-(1-naphthalenyloxy)-N-[7-(1-pyrrolidinyl)-1-oxaspiro[4.5]dec-8-yl]acetamide,

[5R-(5α, 7α, 8β)]-N-Methyl-2-(2-naphthalenyloxy)-N-[7-(1-pyrrolidinyl)-1-oxaspiro[4.5 ]dec-8-yl]acetamide,

[5S-(5α, 7α, 8β)]-N-Methyl-2-(2-naphthalenyloxy)-N-[7-(1-pyrrolidinyl)-1-oxaspiro[4.5]dec-8-yl]acetamide,

[5R-(5α, 7β, 8α)]-N-Methyl-2-(2-naphthalenyloxy)-N-[7-(1-pyrrolidinyl)-1-oxaspiro[4.5]dec-8-yl]acetamide,

[5S-(5α, 7β, 8α)]-N-Methyl-2-(2-naphthalenyloxy)-N- 8 7-(1-pyrrolidinyl)-1-oxaspiro[4.5]dec-8-yl]acetamide,

[5R-(5α, 7α, 8β)]-N-Methyl-N-[7-[methyl-[2-(2-thienyl)ethyl]amino]-1-oxaspiro[4.5]dec-8-yl]-2-(1-naphthalenyloxy) acetamide,

[5S-(5α, 7α, 8β)]-N-Methyl-N-[7-[methyl-[2-(2-thienyl)ethyl]amino]-1-oxaspiro[4.5]dec-8-yl ]-2-(1-naphthalenyloxy) acetamide,

[5R-(5α, 7β, 8α)]-N-Methyl-N-[7-[methyl-[2-(2-thienyl)ethyl]amino]-1-oxaspiro[4.5]dec-8yl]-2-(1-naphthalenyloxy) acetamide,

[5S-(5α, 7β, 8α)]-N-Methyl-N-[7-[methyl-[2-(2-thienyl)ethyl]amino]-1-oxaspiro[4.5]dec-8-yl]-2-(1-naphthalenyloxy) acetamide,

[5R-(5α, 7α, 8β)]-N-Methyl-N-[7-(methyl-2-propenylamino)-1-oxaspiro[4.5]dec-8- yl]-1H-indene-3-acetamide,

[5S-(5α, 7α, 8β)]- N-Methyl-N-[7-(methyl-2-propenyl amino)-1-oxaspiro[4.5]dec-8- yl]-1H-indene-3-acetamide,

[5R-(5α, 7β, 8α)]-N-Methyl-N-[7-(methyl-2-propenylamino)-1-oxaspiro[4.5]dec-8-yl]-1H-indene-3-acetamide,

[5S-(5α, 7β, 8α)]-N-Methyl-N-[7-(methyl-2-propenylamino)-1-oxaspiro[4.5]dec-8-yl]-1H-indene-3-acetamide,

[5R-(5α, 7α, 8β]-N-Methyl-[7-(1-pyrrolidinyl)-amino)-1-oxaspiro[4.5]dec-8-yl]-1H-indene-3 -acetamide,

[5S- 5α, 7α, 8β)]-N-Methyl-[7-(1-pyrrolidinyl)-1-oxaspiro[4.5]dec-8-yl]-1H-indene-3-acetamide,

[5R-5α, 7β, 8α)]-N-Methyl-[7-(1-pyrrolidinyl)-1-oxaspiro[4.5]dec-8-yl]-1H-indene-3-acetamide,

[5S-(5α, 7β, 8α)]-N-Methyl-[7-(1-pyrrolidinyl)-1-1H -indene-3-acetamide,

[5R-(5α, 7α, 8β)]-N-[7-(Dimethylamino)-1-oxaspiro[4.5]dec-8-yl]-N-methyl-1H-indole-3-acetamide,

[5S-(5α, 7α, 8β)]-N-[7-(Dimethylamino)-1-oxaspiro[4.5]dec-8-yl]-N-methyl-1H-indole-3-acetamide,

[5R-(5α, 7β, 8α)]-N-[7-(Dimethylamino)-1-oxaspiro[4.5]dec-8-yl]-N-methyl-1H-indole-3-acetamide,

[5S-(5α, 7β, 8α)]-N-[7-(Dimethylamino)-1 - oxaspiro[4.5]dec-8-yl]-N-methyl-1H-indole-3-acetamide,

[5R-(5α, 7α, 8β)]-N-Methyl-N-[7-(1-pyrrolidinyl)-1-oxaspiro[4.5]dec-8-yl]-1H-indole-3-acetamide,

[5S-(5α, 7α, 8β)]-N-Methyl-N-[7(1-pyrrolidinyl)-1-oxaspiro[4.5]dec-8-yl]-1H-indole-3-acetamide,

[5R-(5α, 7β, 8α)]-N-Methyl-N-[7-(1-pyrrolidinyl)-1-oxaspiro[4.5]dec-8-yl]-1H-indole-3-acetamide,

[5S-(5α, 7β, 8α)]-N-Methyl-N-[7-(1-pyrrolidinyi)-1-oxaspiro[4.5]dec-8-yl]-1H-indole-3-acetamide,

[5R-(5α, 7α, 8β)]-N-Methyl-N-[7-(1-pyrrolidinyl)-1-oxaspiro[4.5]dec-8-yl ]-2- benzofuranacetamide,

[5S-(5α, 7α, 8β)]-N-Methyl-N-[7-(1-pyrrolidinyl)-1-oxaspiro[4.5]dec-8-yl]-2-benzofuranacetamide,

[5R-(5α, 7β, 8α)]-N-Methyl-N-[7-(1-pyrrolidinyl)-1-oxaspiro[4.5]dec-8-yl]-2-benzofuranacetamide,

[5S-(5α, 7β, 8α)]-N-Methyl-N-[7-(1-pyrrolidinyl)-1 -oxaspiro[4.5 ]dec-8-yl]-2- benzofuranacetamide,

[5R-(5α, 7α, 8β)]-N-Methyl-N-[7-(1-pyrrolidinyl)-1-oxaspiro[4.5]dec-8-yl]-3-benzofuranacetamide,

[5S-(5α, 7α, 8β)]-N-Methyl-N-[7-(1-pyrrolidinyl)-1-oxaspiro[4.5]dec-8-yl]-3-benzofuranacetamide,

[5R-(5α, 7β, 8α)]-N-Methyl-N-[7-(1-pyrrolidinyl)-1-oxaspiro[4.5]dec-8-yl]-3-benzofuranacetamide,

[5S-(5α, 7β, 8α)]-N-Methyl-N-[7-(1-pyrrolidinyl)-1-oxaspiro[4.5]dec-8-yl]-3-benzofuranacetamide,

[5R-(5α, 7α, 8β)]-N-Methyl-N-[7-(1-pyrrolidinyl)-1-oxaspiro[4.5]dec-8-yl]-4-benzofuranacetamide,

[5S-(5α, 7α, 8β)]-N-Methyl-N-[7-(1-pyrrolidinyl)-1-oxaspiro[4.5]dec-8-yl]-4-benzofuranacetamide,

[5S-(5α, 7β, 8α)]-N-Methyl-N-[7-(1-pyrrolidinyl)-1-oxaspiro[4.5]dec-8-yl]-4-benzofuranacetamide,

[5R-(5α, 7α, 8β)]-N-[7-[(Cyclopropylmethyl)methylamino]-1-oxaspiro[4.5]dec-8-yl]-N,2-dimethyl-3-benzofuranacetamide,

[5S-(5α, 7α, 8β)]-N-[7-[(Cyclopropylmethyl)methylamino]1-oxaspiro[4.5]dec-8-yl]-N,2-dimethyl-3-benzofuranacetamide,

[5R-(5α, 7β, 8α)]-N-[7-[(Cyclopropylmethyl)methylamino]1-oxaspiro[4.5 ]dec-8-yl]-N,2-dimethyl-3-benzofuranacetamide,

[5S-(5α, 7β, 8α)]-N-[7-[(Cyclopropylmethyl)methylamino]1-oxaspiro[4.5]dec-8-yl]-N,2-dimethyl-3-benzofuranacetamide.

More preferred compounds of the present invention include but are not limited to:

(-) (5α, 7α, 8β)-N-methyl-N-[7-pyrrolidinyl)-1-oxaspiro[4.5]dec-8-yl]-4-benzo[b]furacetamide (Compound I), and (-) - (5α, 7α, 8β)-N-7-(1-pyrrolidinyl)-1-oxaspiro[4.5]-dec-8-yl]-4-benzo[b]thiophene-4-acetamide The compounds of Formula I of the present invention have a very high kappa opioid affinity, selectivity and potency. For example, (-)-(5α-7α-8β)-N-methyl-N-[7-(1-pyrrolidinyl)-1-oxaspiro[4.5]dec-8-yl]-4-benzo[b]furanacetamide gives a Ki of 0.73 nM with a μ/kappa ratio of 798. The MPE$_{50}$ in the rat paw pressure test for analgesia is 0.030 (iv).

This is considerably better than any selective kappa opioid compound known to the inventors.

Current therapies for Parkinson's disease rely on dopamine agonist therapies to replace dopamine depletion in the striatum. However, these treatments are often plagued by debilitating side effects.

One benefit of the instant invention is that relatively low doses of the two drugs can be combined since the effect obtained is synergistic. The compound of Formula I, as illustrated in FIG. 1, potentiates the action of L-DOPA in the animal model where increased locomotor activity is seen. This was accompanied by reductions in rigidity and thus is an anti-Parkinson effect.

METHOD

Rats were rendered Parkinsonian by injection of reserpine (4 mg/kg). This treatment resulted in akinesia and rigidity. Locomotor scores were measured following intraperitoneal injections of (1) L-DOPA, 80 mg/kg, a subthreshold dose; (2) Compound I, 3.25 µg/kg, a subthreshold dose; and (3) a combination of L-DOPA, 80 mg/kg, and Compound I, 3.25 µg/kg. Locomotor scores relate to distance moved by the animals. Following injection of L-DOPA, the animals remained Parkinsonian and attained very low locomotor scores. Following injection of Compound I, the animals remained Parkinsonian and attained very low locomotor scores. With the injection of L-DOPA and Compound I, greatly increased amounts of locomotor activity were seen. These anti-Parkinsonian effects were also accompanied by reductions in rigidity.

Detailed methodologies for the techniques used for the intraperitoneal injections are given in Brotchic JM, et al (*Movement Disorders* 1991;6(2):133–8).

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions, and suspensions and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at least 2% in a primarily liquid composition. The most satisfactory compositions are those in which a much higher proportion of the active ingredient is present.

For the therapeutic uses described above, the mammalian dosage range of the combination is about 1 to about 25 µg of a compound of Formula I and an amount 1/10 to ½ the normal clinical dose of L-DOPA. The usual and/or initial dose for L-DOPA is 0.5 to 1.0 g daily total given in two or more divided doses daily. If this amount is tolerated, the dose is increased by 0.50 to 0.75 g daily. This increased dose is held for from then to 7 days for tolerance. The final dose is usually about 8.0 g daily. Determination of the proper dosage for a particular situation is within the skill of the art.

Routes of administration of the subject compounds of Formula I or salts thereof are oral, parenteral, transdermal, or intranasalo For example, a useful intravenous dose is between 0.001 and 10 mg/kg. A preferred intravenous dose is 0.01 to 1 mg/kg. A still further preferred dose is 0.01 to 0.55 mg/kg. A useful oral dose is 0.01 to 30 mg/kg.

The following examples of formulations are provided to enable one skilled in the art to practice the invention. These examples are not intended to limit the scope of the invention in any way but rather to be illustrative thereof. Compound I is a compound of Formula I as described hereinbefore.

EXAMPLE 1

Injectables

Compound I, Water for injection USP q.s. and L-DOPA

The hydrochloride salt of Compound I is dissolved in water and passed through a 0.2-micron filter. Aliquots of the filtered solution are added to ampoules or vials, sealed, and sterilized.

EXAMPLE 2

| Syrups 2 mg Compound I and L-DOPA/5-mL syrup | |
|---|---|
| Compound I and L-DOPA | 12.5 g |
| Purified Water USP | 200 mL |
| Cherry Syrup qu | 1000 mL |

Compound I and L-DOPA are dissolved in the water and to this solution the syrup is added with mild stirring.

EXAMPLE 3

| Capsules 0.5 mg, 1 mg, or 2 mg | |
|---|---|
| Compound I and L-DOPA | 250 g |
| Lactose USP, Anhydrous q.s. or | 250 g |
| Sterotex Powder HM | 5 g |

Combine Compound I and L-DOPA and the lactose in a tumble, blend for 2 minutes, blend for 1 minute with the intensifier bar, and then tumble blend again for 1 minute. A portion of the blend is then mixed with the Sterotex Powder, passed through a #30 screen and added back to the remainder of the blend. The mixed ingredients are then blended for 1 minute, blended with the intensifier bar for 30 seconds, and tumble-blended for an additional minute. The appropriately sized capsules are filled with 141 mg, 352.5 mg, or 705 mg of the blend, respectively, for the 50-mg, 125-mg, and 250-mg containing capsules.

EXAMPLE 4

| Tablets 0.5 mg, 1 mg, or 2 mg | |
|---|---|
| Compound I and L-DOPA | 125 g |
| Corn Starch NF | 200 g |
| Cellulose, Microcrystalline | 46 g |
| Sterotex Powder HM | 4 g |
| Purified Water q.s. or | 300 mL |

Combine the corn starch, the cellulose, Compound I and L-DOPA, together in a planetary mixer and mix for 2 minutes. Add the water to this combination and mix for 1 minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for 5 minutes by drum rolling. Compressed tablets of 0.150 mg, 3.75 mg, and 7.50 mg, respectively, of the total mix are formed with appropriate sized punches the 0.50 mg, 1.25 mg, or 5.00 mg containing tablets.

I claim:

1. A pharmaceutical composition for treating Parkinson's disease comprising from 1 to 25 μg of a compound of formula

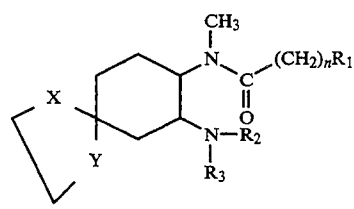
I or a pharmaceutically acceptable salt thereof wherein n is an integer of from 1 to 6; either of X or Y is oxygen and the other is —CH$_2$—; R$_1$ is selected from

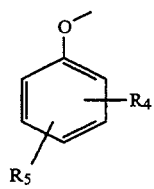
a)

where R$_4$ and R$_5$ are independently hydrogen, fluorine, chlorine, bromine, nitro, trifluoromethyl, alkyl of from 1 to 6 carbon atoms, alkoxy of from 1 to 6 carbon atoms, or aryl;

b) 3,4,5-trimethylphenoxy;

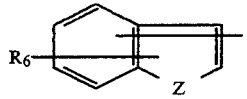
c)

where R$_6$ is hydrogen, fluorine, chlorine, alkyl of from 1 to 6 carbon atoms, or aryl; Z is —CH$_2$—, —O—, —S—, or —NR$_7$— where R$_7$ is hydrogen, alkanoyl of from 1 to 6 carbon atoms, or alkyl of from 1 to 6 carbon atoms;

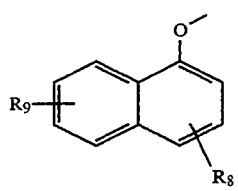
d)

wherein R$_8$ and R$_9$ are independently hydrogen, fluorine, bromine, alkyl of from 1 to 6 carbon atoms, or alkoxy of from 1 to 4 carbon atoms; or

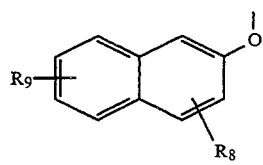
e)

where R$_8$ and R$_9$ are as defined above; where R$_2$ is methyl and R$_3$ is hydrogen, aikyl of from 1 to 6 carbon atoms,

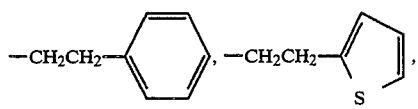

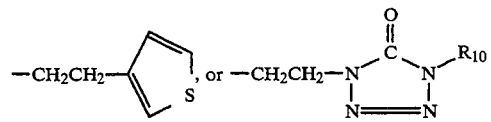

where R$_{10}$ is alkyl of from 1 to 4 carbon atoms; or where R$_2$ and R$_3$ when taken together with the nitrogen atom to which they are attached, form a pyrrolidinyl, piperidinyl, or hexahydro-1H-azepinyl ring
and 0.8 to 4.0 g of L-DOPA or a pharmaceutically acceptable salt thereof in admixture with a pharmaceutically acceptable carrier.

2. A method for treating Parkinson's disease which comprises administering to a patient in need of said treatment a synergistic pharmaceutical composition comprising therapeutically effective amount of L-DOPA or a pharmaceutically acceptable salt thereof and a therapeutically effective amount of a compound of formula

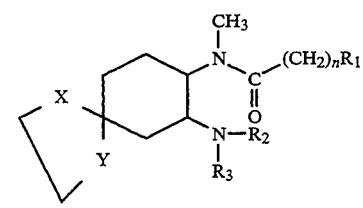
I or a pharmaceutically acceptable salt thereof wherein n is an integer of from 1 to 6; either of X or Y is oxygen and the other is —CH$_2$—; R$_1$ is selected from

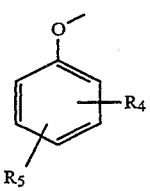
a)

where R$_4$ and R$_5$ are independently hydrogen, fluorine, chlorine, bromine, nitro, trifluoromethyl, alkyl of from 1 to 6 carbon atoms, alkoxy of from 1 to 6 carbon atoms, or aryl;

b) 3,4,5-trimethylphenoxy;

c) 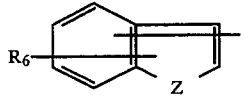

where $R_6$ is hydrogen, fluorine, chlorine, alkyl of from 1 to 6 carbon atoms, or aryl; Z is —CH$_2$—, —O—, —S—, or —NR$_7$— where $R_7$ is hydrogen, alkanoyl of from 1 to 6 carbon atoms, or alkyl of from 1 to 6 carbon atoms;

d) 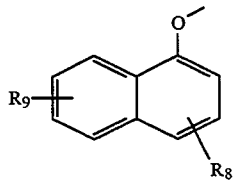

wherein $R_8$ and $R_9$ are independently hydrogen, fluorine, bromine, alkyl of from 1 to 6 carbon atoms, or alkoxy of from 1 to 4 carbon atoms; or e) 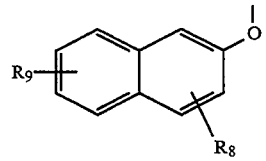

where $R_8$ and $R_9$ are as defined above; where $R_2$ is methyl and $R_3$ is hydrogen, alkyl of from 1 to 6 carbon atoms,

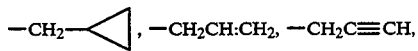

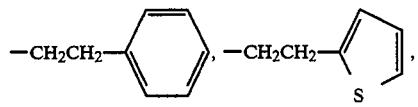

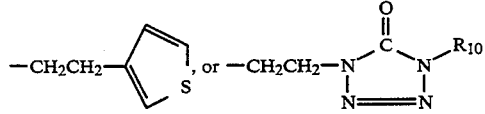

where $R_{10}$ is alkyl of from 1 to 4 carbon atoms; or where $R_2$ and $R_3$ when taken together with the nitrogen atom to which they are attached, form a pyrrolidinyl, piperidinyl, or hexahydro-1H-azepinyl ring.

3. A method according to claim 2 wherein the compounds are (-)-5α-7α-8β-N-methyl-N-[7-(1-pyrrolidinyl)-1-oxaspiro [4.5]dec-8-yl]-4-benzofuranacetamide and L-DOPA.

4. A method according to claim 2 wherein 1 to 25 µg of (-)-5α-7α-8β-N-methyl-N-[7-(1-pyrrolidinyl)-1-oxaspiro [4.5]dec-8-yl]-4-benzofuranacetamide and 0.8 to 4 g of L-DOPA or a pharmaceutically acceptable salt is administered.

* * * * *